(12) United States Patent
Xu et al.

(10) Patent No.: US 6,509,347 B2
(45) Date of Patent: Jan. 21, 2003

(54) CRYSTALLINE FORMS OF AN INTEGRIN RECEPTOR ANTAGONIST

(75) Inventors: Wei Xu, North Wales, PA (US); Yaling Wang, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/167,678

(22) Filed: Jun. 11, 2002

(65) Prior Publication Data

US 2002/0188001 A1 Dec. 12, 2002

Related U.S. Application Data

(60) Provisional application No. 60/297,393, filed on Jun. 11, 2001.

(51) Int. Cl.$^7$ .................. A61K 31/4375; C07D 471/04

(52) U.S. Cl. ........................................ 514/300; 546/122
(58) Field of Search ............................ 514/300; 546/122

(56) References Cited

U.S. PATENT DOCUMENTS 6,017,926 A   1/2000   Akew et al.

FOREIGN PATENT DOCUMENTS

WO      WO 01/34602 A2      5/2001

*Primary Examiner*—Patricia L. Morris
(74) *Attorney, Agent, or Firm*—Patricia A. Shatynski; Mark R. Daniel

(57) ABSTRACT

The present invention relates to novel crystalline forms of the integrin αvβ3 antagonist 3-{2-oxo-3-[3-(5,6,7,8-tetrahydro-[1,8]naphthyridin-2-yl)-propyl]imidazolidin-1-yl}-3(S)-(6-methoxy-pyridin-3-yl)-propionic acid.

19 Claims, 8 Drawing Sheets

CRYSTALLINE FORMS OF AN INTEGRIN RECEPTOR ANTAGONIST

CROSS-REFERENCE TO RELATED APPLICATIONS

The present invention is related to U.S. provisional application Serial No. 60/297,393, filed Jun. 11, 2001, the contents of which are hereby incorporated by reference.

BACKGROUND OF THE INVENTION

U.S. Pat. No. 6,017,926 (issued Jan. 25, 2000) discloses the compound of structural formula I:

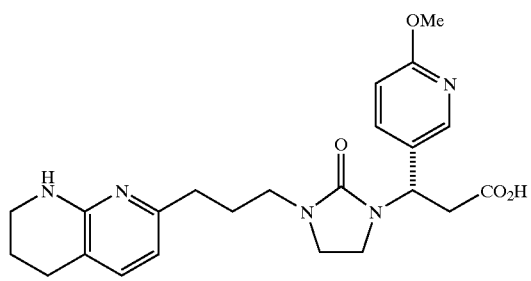

Compound I is an antagonist of the integrin $\alpha v\beta 3$ receptor and is useful for inhibiting bone resorption, restenosis, angiogenesis, diabetic retinopathy, macular degeneration, inflammatory arthritis, cancer, and metastatic tumor growth. It is particularly useful for inhibiting bone resorption and for the treatment and prevention of osteoporosis. There is no specific disclosure or discussion in U.S. Pat. No. 6,017,926 of crystalline forms of compound I. A novel process for the preparation of compound I was disclosed in WO 01/34602 (May 17, 2001). The latter process yielded compound I in the form of a crystalline hemihydrate as characterized by differential scanning calorimetry, X-ray powder diffraction, and FT-infrared spectroscopy. However, the sensitivity of the hemihydrate form to moisture complicates the development of solid dosage formulations for compound I. It is therefore desirable to have available other crystalline forms of compound I having improved physical and chemical stability and hence greater suitability for the preparation of solid pharmaceutical dosage forms containing the pharmacologically active ingredient.

SUMMARY OF THE INVENTION

The present invention is concerned with novel crystalline forms of the integrin $\alpha v\beta 3$ receptor antagonist 3-{2-oxo-3-[3-(5,6,7,8-tetrahydro-[1,8]naphthyridin-2-yl)-propyl]imidazolidin-1-yl}-3(S)-(6-methoxy-pyridin-3-yl)-propionic acid (I). These crystalline forms are new and may have advantages in the preparation of pharmaceutical compositions of compound I, such as ease of processing, handling, or dosing. In particular, they may improved physiochemical properties such as solubility, stability, or rate of solution, rendering them particularly suitable for the manufacture of dosage forms. The invention also concerns pharmaceutical compositions containing the novel crystalline forms as well methods for using them as $\alpha v\beta 3$ integrin receptor antagonists.

DETAILED DESCRIPTION OF THE INVENTION

The present invention provides 3-{2-oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of a crystalline anhydrate.

The present invention also provides 3-{2-oxo-3-[3-(5,6,7,8-tetrahydro-[1,8]naphthyridin-2-yl)-propyl]imidazolidin-1-yl }-3(S)-(6-methoxy-pyridin-3-yl)-propionic acid in the form of a crystalline dihydrate.

The present invention also provides 3-{2-oxo-3-[3-(5,6,7,8-tetrahydro-[1,8]naphthyridin-2-yl)-propyl]imidazolidin-1-yl }-3(S)-(6-methoxy-pyridin-3-yl)-propionic acid in the form of a crystalline tetrahydrate.

The present invention also provides 3-{2-oxo-3-[3-(5,6,7,8-tetrahydro-[1,8]naphthyridin-2-yl)-propyl]imidazolidin-1-yl }-3(S)-(6-methoxy-pyridin-3-yl)-propionic acid in the form of a crystalline pentahydrate.

X-ray powder diffraction studies are widely used to characterize molecular structures, crystallinity, and polymorphism. All X-ray patterns, except for the crystalline anhydrate, were collected using a Siemens D5000 X-ray diffractometer, using Cu K$\alpha$ radiation. The patterns were collected on a powder sample of compound I subject to different relative humidities controlled by a Relative Humidity generator from VTI Corporation. The X-ray powder diffraction pattern of the crystalline anhydrate was generated on a Philip Analytical X-ray instrument with XRG 3100 control and PW 3710 mpd control. Cupper K-Alpha 1 radiation was used as the source.

Figure 1:
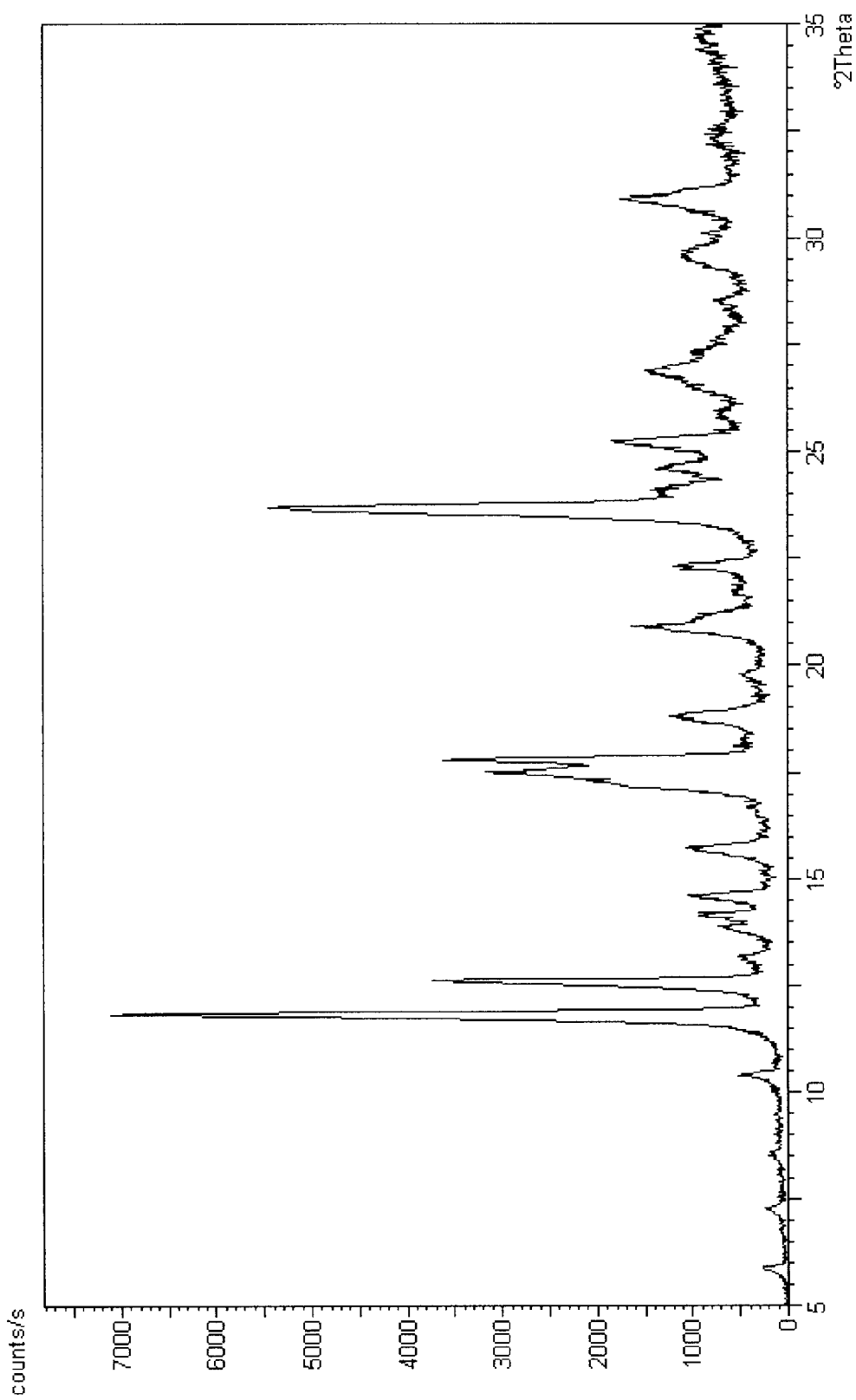
FIG. 1 is a characteristic X-ray diffraction pattern of the crystalline anhydrate of compound I.

FIG. 1 shows the X-ray diffraction pattern for the anhydrate form of compound I. The anhydrate exhibited characteristic diffraction peaks corresponding to d-spacings of 8.52, 7.46, 7.01, 5.07, 4.98, 4.70, 4.25, 3.75, and 3.53 angstroms.

Figure 2:
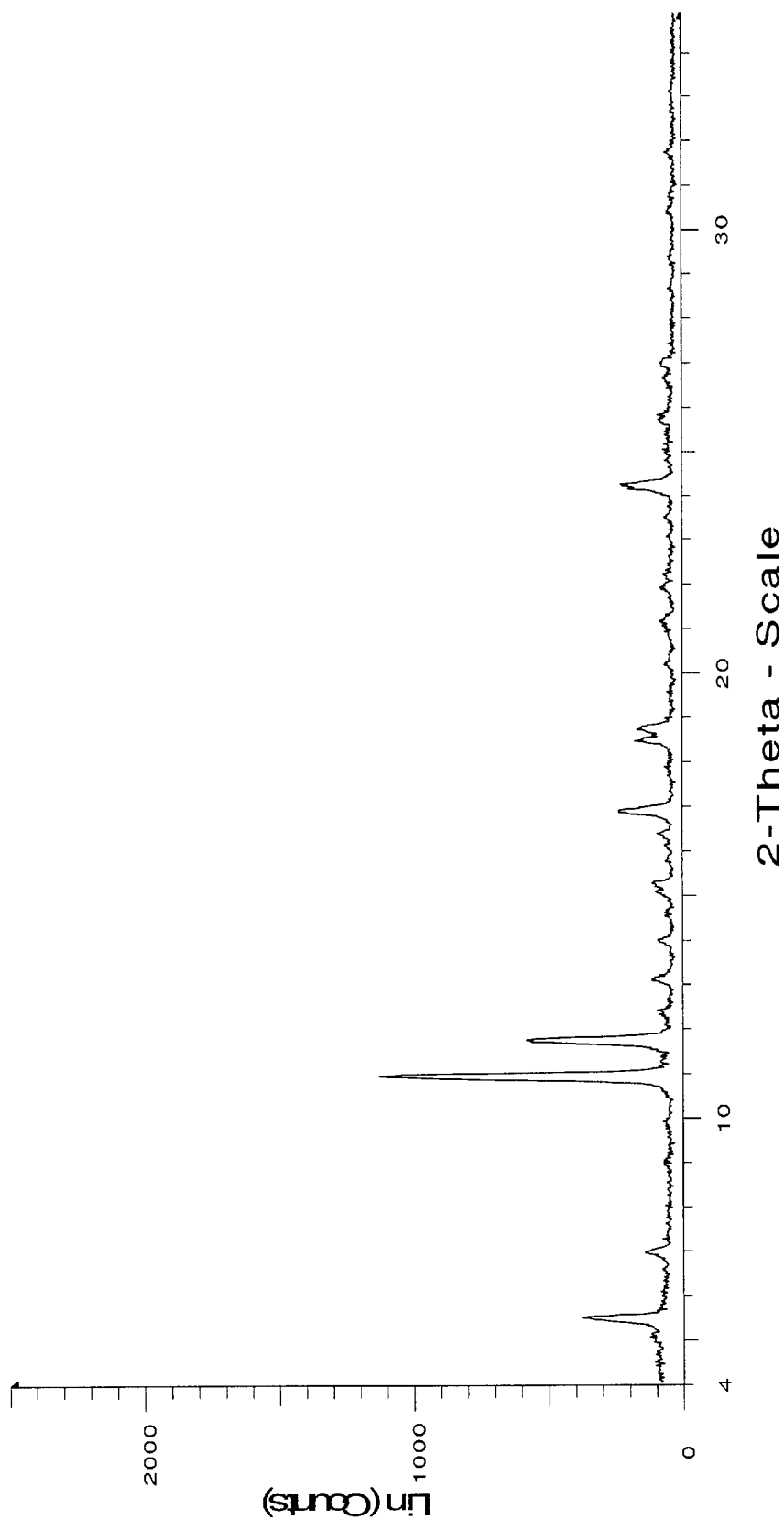
FIG. 2 is a characteristic X-ray diffraction pattern of the crystalline dihydrate of compound I.

FIG. 2 shows the X-ray diffraction patttern for the dihydrate form of compound I. The dihydrate exhibited characteristic diffraction peaks corresponding to d-spacings of 16.18, 12.72, 8.11, 7.54, 5.25, 4.79, 4.73, and 3.67 angstroms.

Figure 3:
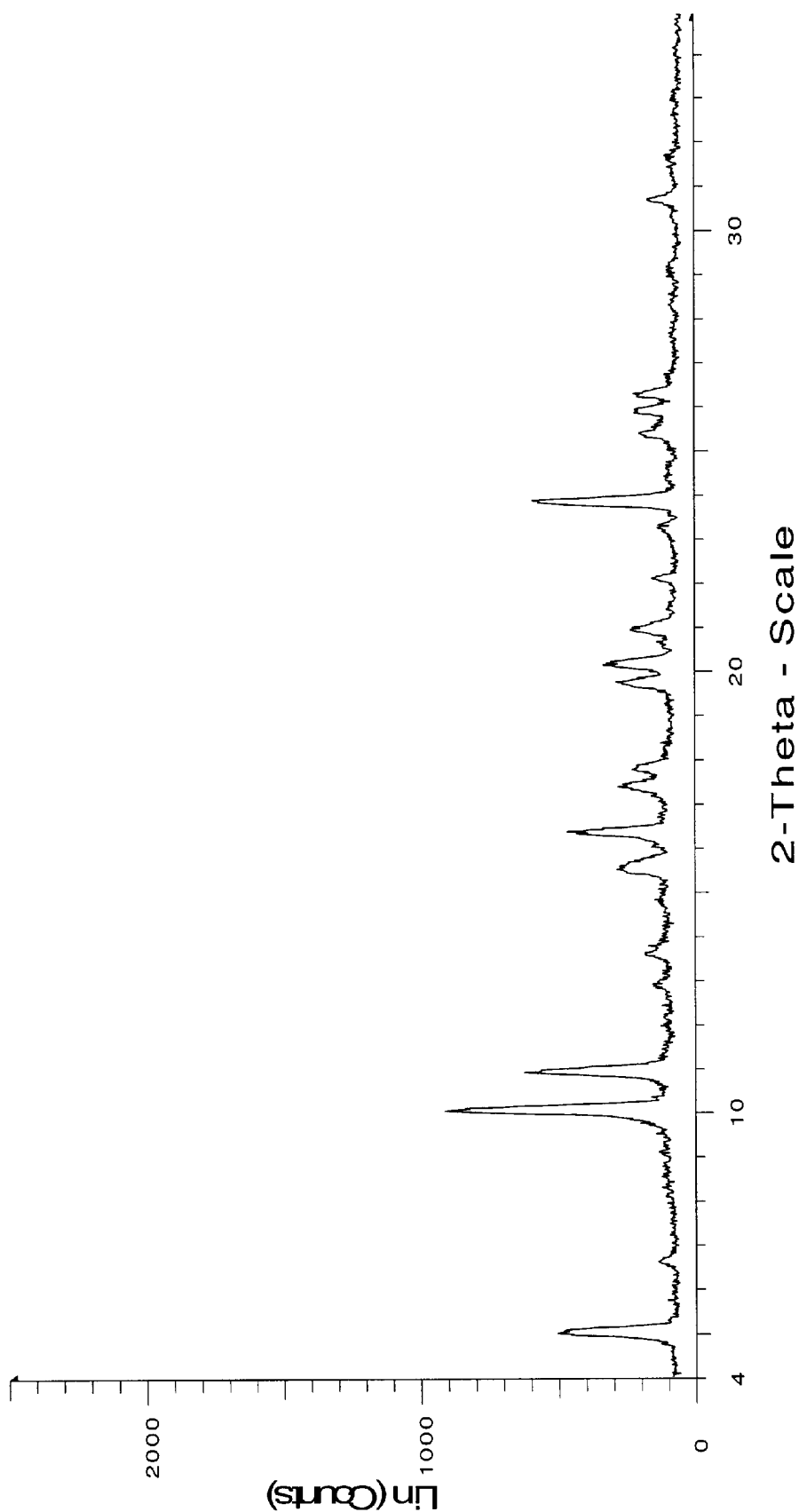
FIG. 3 is a characteristic X-ray diffraction pattern of the crystalline tetrahydrate of compound I.

FIG. 3 shows the X-ray diffraction patttern for the tetrahydrate form of compound I. The tetrahydrate exhibited characteristic diffraction peaks corresponding to d-spacings of 17.61, 13.35, 8.80, 8.09, 5.70, 5.42, 5.09, 4.95, 4.50, 4.40, and 3.73 angstroms.

Figure 4:
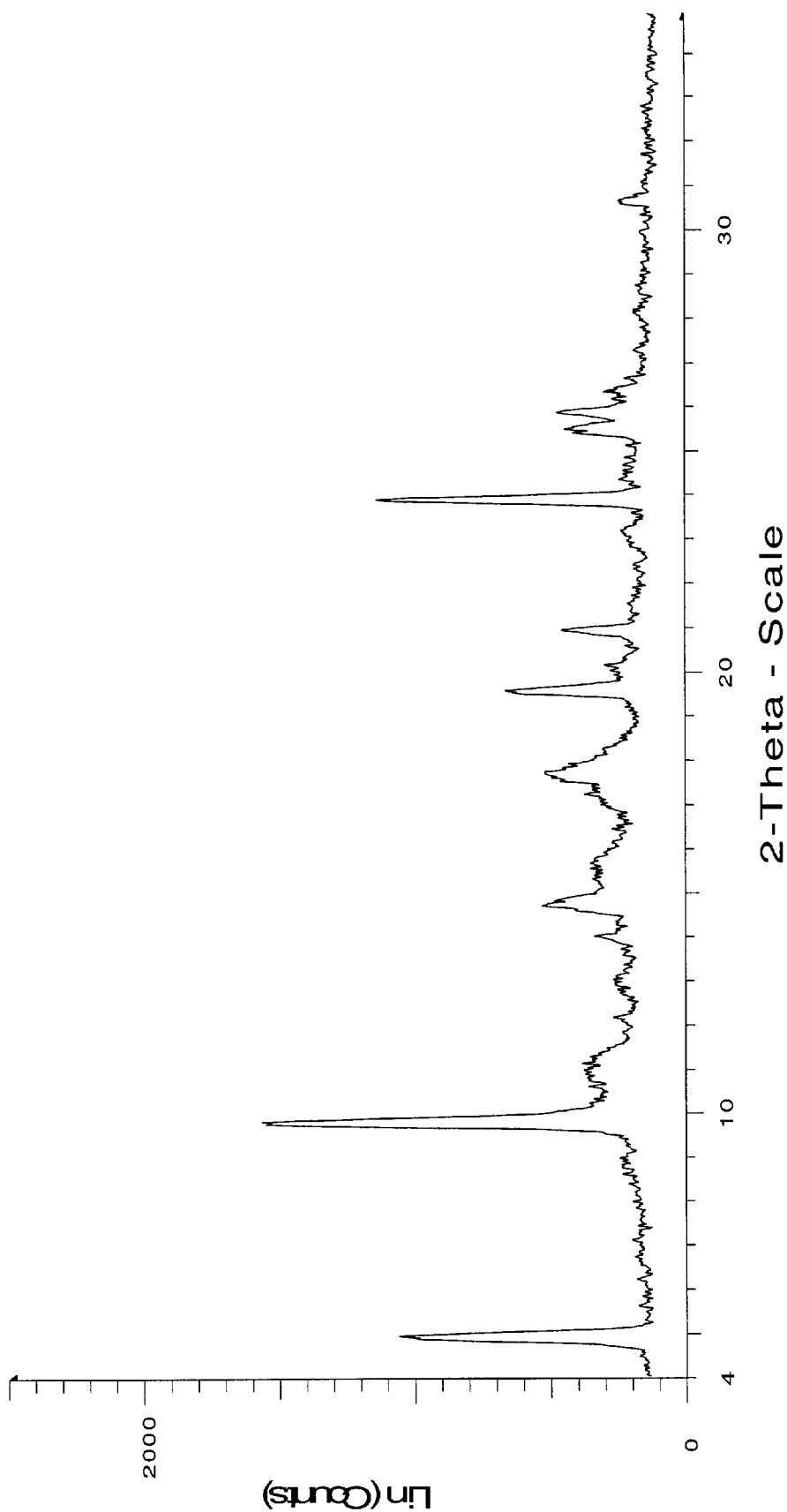
FIG. 4 is a characteristic X-ray diffraction pattern of the crystalline pentahydrate of compound I.

FIG. 4 shows the X-ray diffraction pattern for the pentahydrate form of compound I. The pentahydrate exhibited characteristic diffraction peaks corresponding to d-spacings of 18.05, 9.05, 4.53, 4.24, and 3.72 angstroms.

In addition to the X-ray powder diffraction patterns described above, the various novel crystalline forms of compound I were further characterized by their solid-state carbon-13 nuclear magnetic resonance (NMR) spectra. The solid-state carbon-13 NMR spectra were obtained on a Bruker DSX 400WB NMR system using a Bruker 7 mm double resonance CPMAS probe. The NMR spectra utilized proton/carbon-13 cross-polarization magic-angle spinning with variable-amplitude cross polarization and total sideband suppression. The samples were spun at 7.0 kHz, and a total of between 162 and 1024 scans were collected with a recycle delay of 10 seconds. A line broadening of 20 Hz was applied to the spectra before FT was performed. Chemical shifts are reported on the TMS scale using the carbonyl carbon of glycine (176.03 p.p.m.) as a secondary reference. The spectrum for the anhydrate form was obtained at a sample temperature of 80° C.

Figure 6:
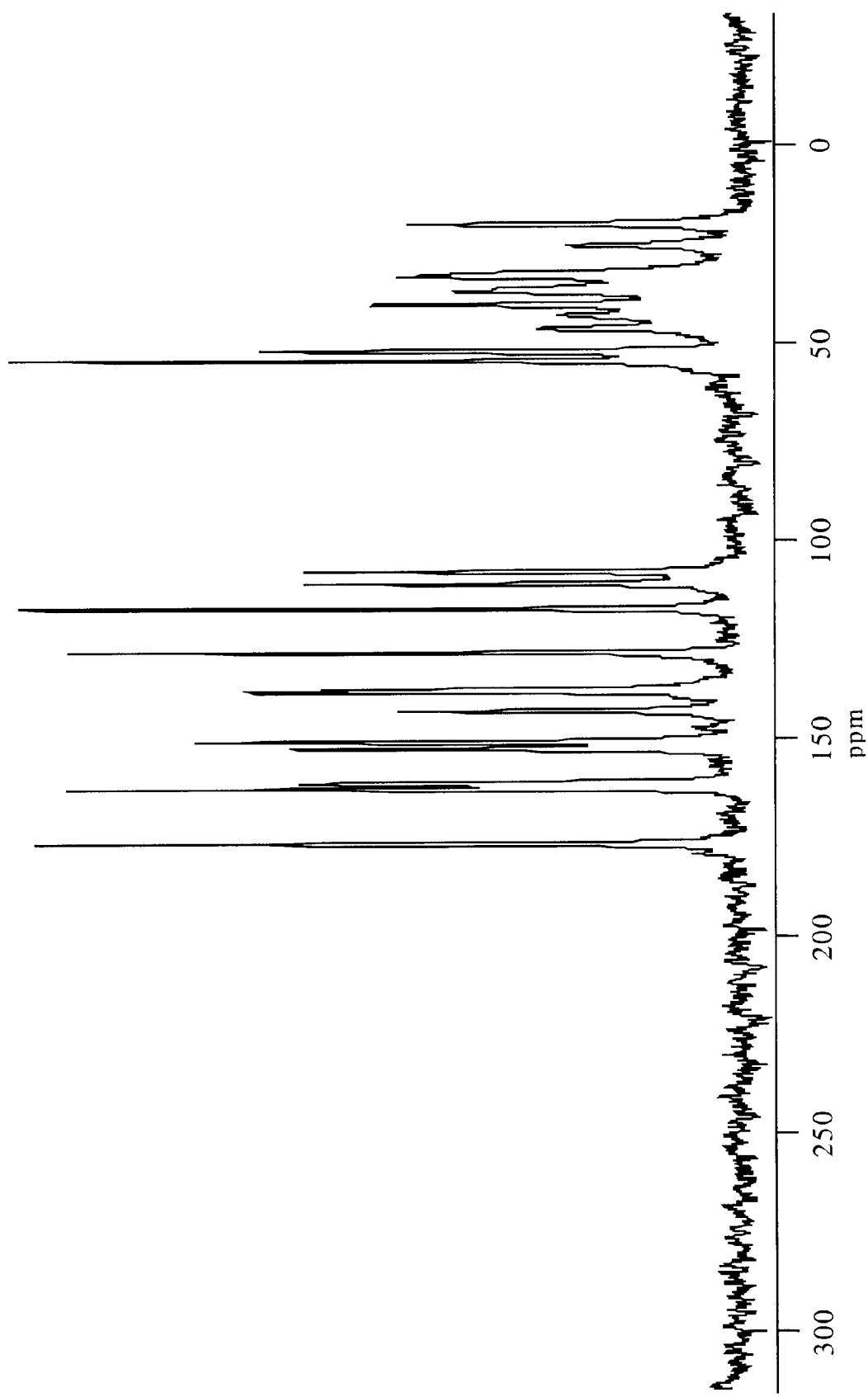
FIG. 6 is a carbon-13 cross-polarization magic-angle spinning (CPMAS) nuclear magnetic resonance (NMR) spectrum of the crystalline anhydrate of compound I.

FIG. 6 shows the solid-state carbon-13 CPMAS NMR spectrum for the anhydrate form of compound I. The anhydrate form exhibited characteristic signals with chemical shift values of 176.8, 161.5, 152.8, 54.8, 40.6, 37.1, and 20.0 p.p.m. Further characteristic of the anhydrate form are the signals with chemical shift values of 162.9, 150.9, 143.2, 138.4, 111.0, 43.3, and 33.3 p.p.m. Even further characteristic of the anhydrate form are the signals with chemical shift values of 128.4, 117.1, 46.5, and 25.4 p.p.m.

Figure 7:
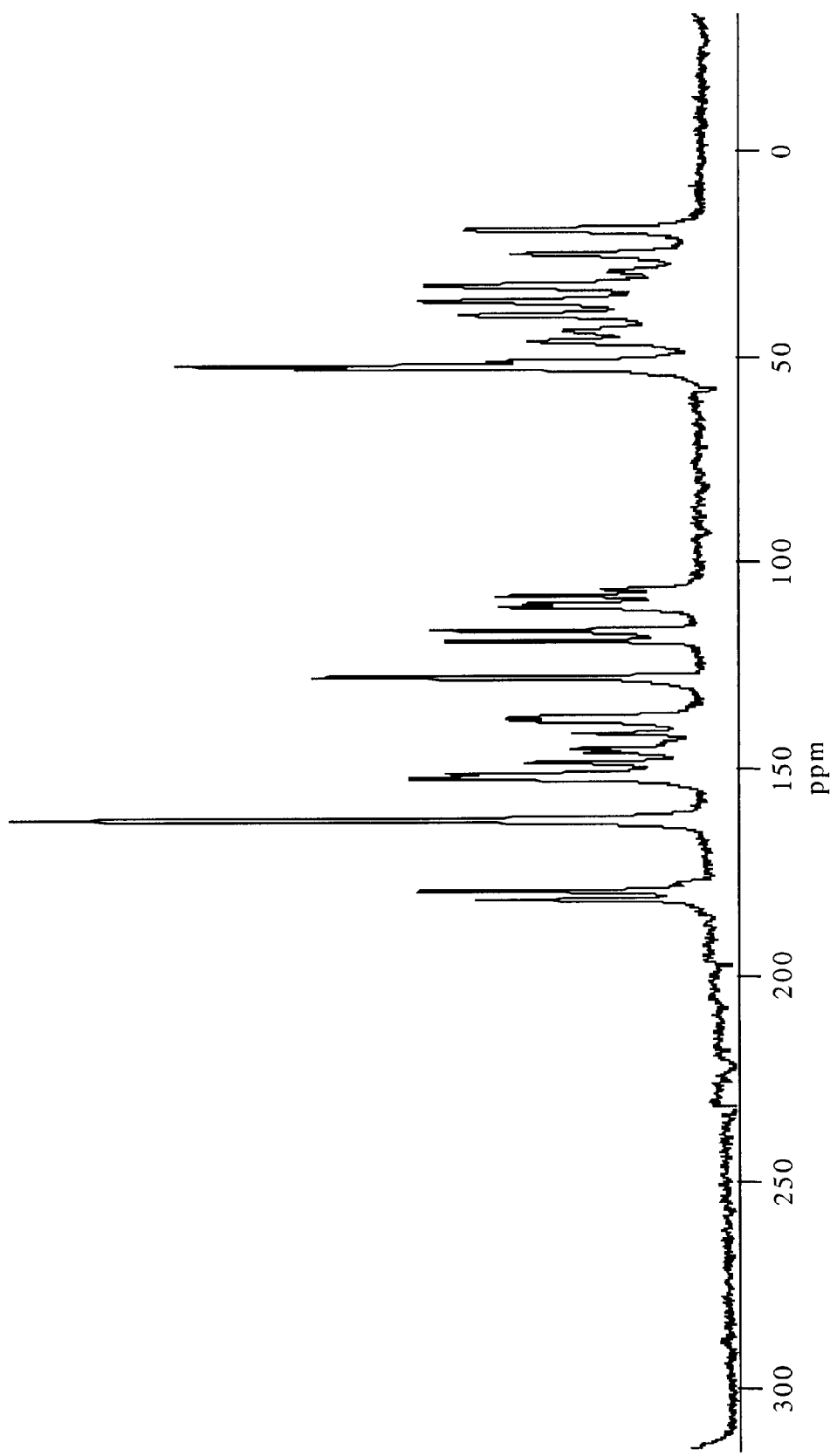
FIG. 7 is a carbon-13 cross-polarization magic-angle spinning (CPMAS) nuclear magnetic resonance (NMR) spectrum of the crystalline dihydrate of compound I.

FIG. 7 shows the solid-state carbon-13 CPMAS NMR spectrum for the dihydrate form of compound I. The dihydrate form exhibited characteristic signals with chemical shift values of 145.9, 145.0, 137.5, 110.0, 106.3, and 51.0 p.p.m. Further characteristic of the dihydrate form are the signals with chemical shift values of 181.5, 162.2, 52.9, 32.7, 29.2, and 25.0 p.p.m. Even further characteristic of the dihydrate form are the signals with chemical shift values of 152.1, 151.1, 148.3, 141.2, 118.8, and 43.6 p.p.m.

Figure 8:
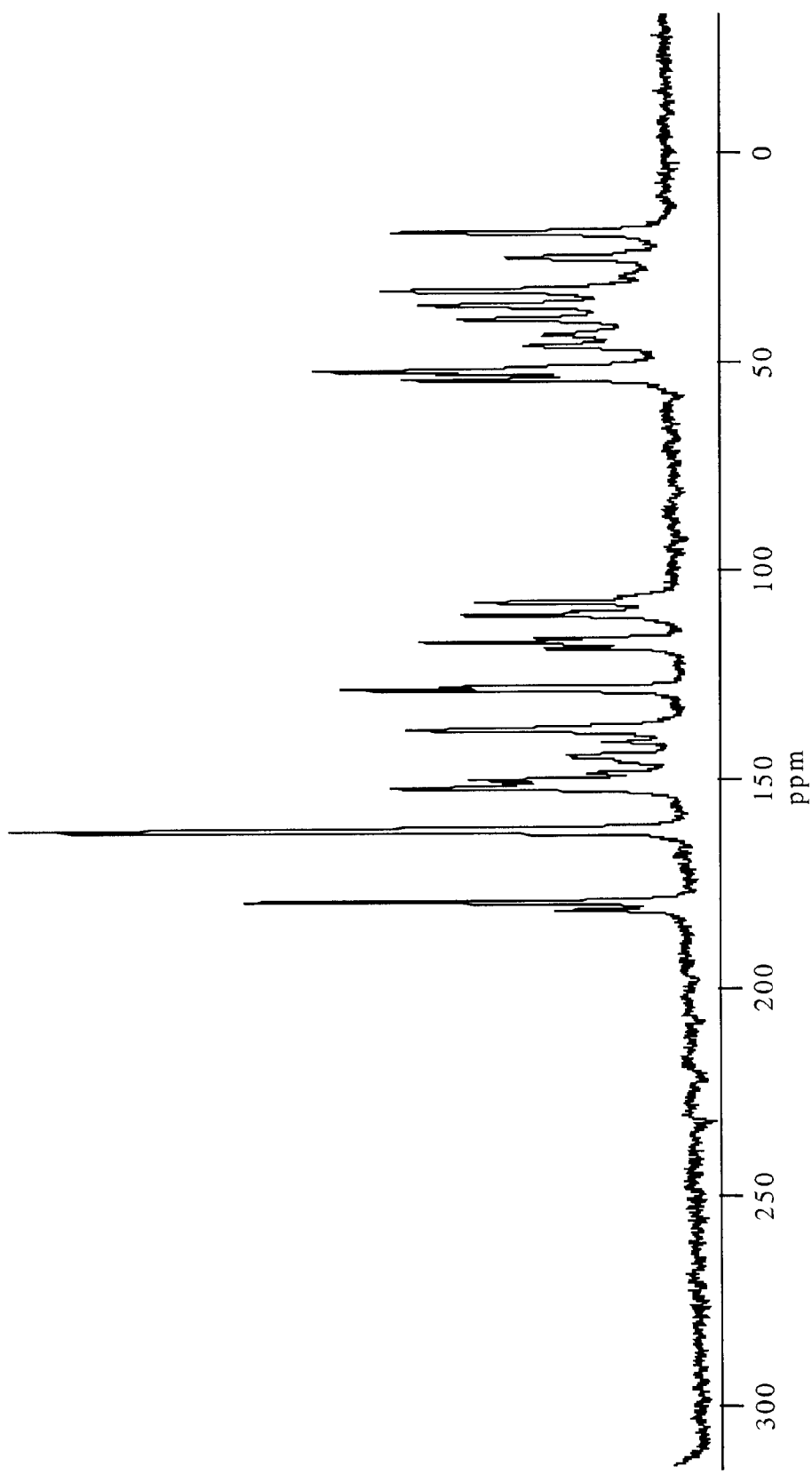
FIG. 8 is a carbon-13 cross-polarization magic-angle spinning (CPMAS) nuclear magnetic resonance (NMR) spectrum of the crystalline tetrahydrate of compound I.

FIG. 8 shows the solid-state carbon-13 CPMAS NMR spectrum for the tetrahydrate form of compound I. The tetrahydrate form exhibited characteristic signals with chemical shift values of 150.1, 144.2, and 107.6 p.p.m. Further characteristic of the tetrahydrate form are the signals with chemical shift values of 181.3, 162.4, 54.2, 52.8, 32.9, 29.4, and 25.2 p.p.m. Even further characteristic of the tetrahydrate form are the signals with chemical shift values of 152.0, 151.0, 148.4, 141.1, 128.5, 118.7, 117.2, and 43.5 p.p.m.

The novel polymorphs of the present invention were obtained in the following fashion starting with the hemihydrate disclosed in WO 01/34602, which was prepared by drying compound I crystallized from water to a moisture content of about 2% as determined by Karl Fisher titration. The hemihydrate was subjected to various relative humidities. The anhydrate form of compound I was generated by drying the hemihydrate to 0% moisture level. The dihydrate form was prepared by equilibrating the hemihydrate form at ambient temperature and 60% relative humidity. The tetrahydrate form was prepared by equilibrating the hemihydrate form at ambient temperature and 75% relative humidity. The pentahydrate form was prepared by equilibrating the hemihydrate form at ambient temperature and 85% relative humidity.

Figure 5:
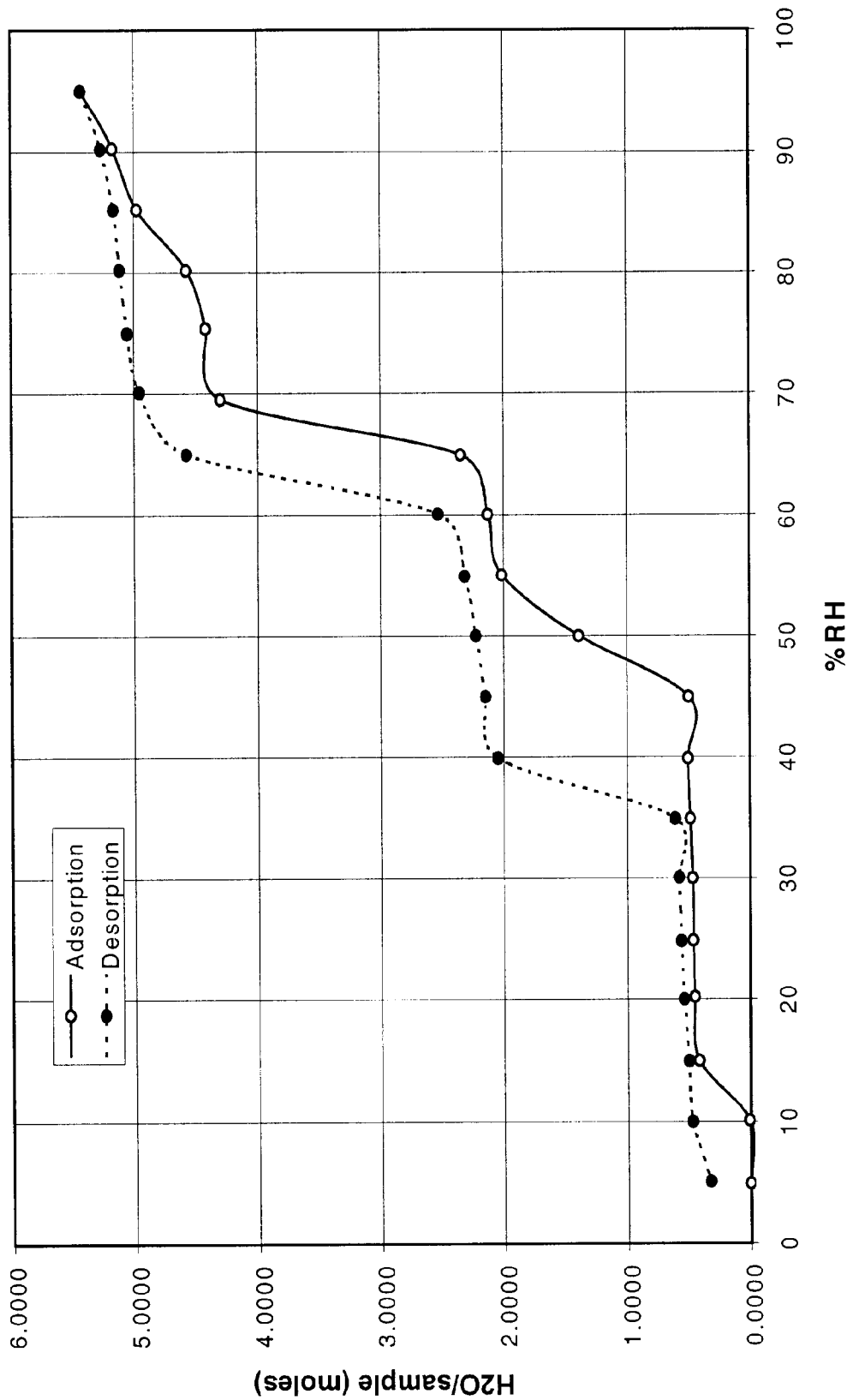
FIG. 5 shows the moisture adsorption and desorption curves for compound I at 25° C.

FIG. 5 shows the moisture adsorption and desorption curves of the hemihydrate at 25° C. The moisture isotherms were obtained on a MB-300W moisture balance by VTI Corporation. Five distinct plateau regions with a water to drug ratio of 0, 0.5, 2.0, 4.5, and 5 were identified. The X-ray powder diffraction patterns of the compound equilibrated at 5, 35, 60, 75, and 85% RH were collected, and four distinct powder patterns were observed. Based on the water content associated with each powder pattern, the hemihydrate, dihydrate, tetrahydrate, and pentahydrate forms of compound I were identified. The anhydrate pattern was collected on a hot-stage X-ray, where the sample was held at 75° C. while the data were collected.

Another aspect of the present invention provides a method for the treatment and/or prevention of clinical conditions for which an integrin αvβ3 receptor antagonist is indicated, which method comprises administering to a patient in need of such prevention or treatment a prophylactically or therapeutically effective amount of the anhydrate, dihydrate, tetrahydrate, or pentahydrate crystalline form of compound I. Such clinical conditions include the inhibition of bone resorption, the treatment and/or prevention of osteoporosis, and the inhibition of vascular restenosis, diabetic retinopathy, macular degeneration, atherosclerosis, inflammatory arthritis, cancer, and metastatic tumor growth. Inflammatory arthritis encompasses both rheumatoid arthritis and osteoarthritis.

The present invention also provides the use of the anhydrate, dihydrate, tetrahydrate, or pentahydrate crystalline form of compound I for the manufacture of a medicament for the prevention and/or treatment of clinical conditions for which an antagonist of the integrin αvβ3 receptor is indicated.

The present invention provides a pharmaceutical composition comprising the anhydrate, dihydrate, tetrahydrate, or pentahydrate crystalline form of compound I, in association with one or more pharmaceutically acceptable carriers.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion.

Advantageously, the crystalline forms of the present invention may be administered in a single daily dose, or the total daily dosage may be administered in divided doses of two, three or four times daily. Furthermore, the crystalline forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the crystalline forms herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug component can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The various crystalline forms of compound I disclosed in the present invention can be made as described above. Precise details of the conditions, and obvious modifications of the procedures, are well within the capabilities of the skilled person in the art.

EXAMPLE OF A PHARMACEUTICAL FORMULATION

The dihydrate form of compound I is formulated into a tablet by a direct compression process. A 100 mg potency tablet is composed of 108 mg of the active, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

What is claimed is:

1. 3-{2-Oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of an anhydrate.

2. 3-{2-Oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of a dihydrate.

3. 3-{2-Oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of a tetrahydrate.

4. 3-{2-Oxo-3-[3-(5,6,7,8-tetrahydro-[1,8]naphthyridin-2-yl)-propyl]imidazolidin-1-yl}-3(S)-(6-methoxy-pyridin-3-yl)-propionic acid in the form of a pentahydrate.

5. The anhydrate of claim 1 characterized by characteristic absorption bands obtained from the X-ray powder diffraction pattern at spectral d-spacings of 8.52, 7.46, 7.01, 5.07, 4.98, 4.70, 4.25, 3.75, and 3.53 angstroms.

6. The dihydrate of claim 2 characterized by characteristic absorption bands obtained from the X-ray powder diffraction pattern at spectral d-spacings of 16.18, 12.72, 8.11, 7.54, 5.25, 4.79, 4.73, and 3.67 angstroms.

7. The tetrahydrate of claim 3 characterized by characteristic absorption bands obtained from the X-ray powder diffraction pattern at spectral d-spacings of 17.61, 13.35, 8.80, 8.09, 5.70, 5.42, 5.09, 4.95, 4.50, 4.40, and 3.73 angstroms.

8. The pentahydrate of claim 4 characterized by characteristic absorption bands obtained from the X-ray powder diffraction pattern at spectral d-spacings of 18.05, 9.05, 4.53, 4.24, and 3.72 angstroms.

9. The anhydrate of claim 1 having the solid-state carbon-13 nuclear magnetic resonance spectrum shown in FIG. 6.

10. The dihydrate of claim 2 having the solid-state carbon-13 nuclear magnetic resonance spectrum shown in FIG. 7.

11. The tetrahydrate of claim 3 having the solid-state carbon-13 nuclear magnetic resonance spectrum shown in FIG. 8.

12. A pharmaceutical composition comprising a prophylactically or therapeutically effective amount of the anhydrate according to claim 1 in association with one or more pharmaceutically acceptable carriers.

13. A pharmaceutical composition comprising a prophylactically or therapeutically effective amount of the dihydrate according to claim 2 in association with one or more pharmaceutically acceptable carriers.

14. A pharmaceutical composition comprising a prophylactically or therapeutically effective amount of the tetrahydrate according to claim 3 in association with one or more pharmaceutically acceptable carriers.

15. A pharmaceutical composition comprising a prophylactically or therapeutically effective amount of the pentahydrate according to claim 4 in association with one or more pharmaceutically acceptable carriers.

16. A method for the prevention and/or treatment of osteoporosis comprising administering to a patient in need of such prevention or treatment a prophylactically or therapeutically effective amount of the anhydrate according to claim 1.

17. A method for the prevention and/or treatment of osteoporosis comprising administering to a patient in need of such prevention or treatment a prophylactically or therapeutically effective amount of the dihydrate according to claim 2.

18. A method for the prevention and/or treatment of osteoporosis comprising administering to a patient in need of such prevention or treatment a prophylactically or therapeutically effective amount of the tetrahydrate according to claim 3.

19. A method for the prevention and/or treatment of osteoporosis comprising administering to a patient in need of such prevention or treatment a prophylactically or therapeutically effective amount of the pentahydrate according to claim 4.

* * * * *